(12) United States Patent
Uihlein

(10) Patent No.: US 10,946,173 B2
(45) Date of Patent: *Mar. 16, 2021

(54) HAND-OPERATED FUNCTIONAL HOSE INSTRUMENT

(71) Applicant: EPflex Feinwerktechnik GmbH, Dettingen/Erms (DE)

(72) Inventor: Bernhard Uihlein, Dettingen (DE)

(73) Assignee: EPflex Feinwerktechnik GmbH, Dettingen (DE)

( * ) Notice: Subject to any disclaimer, the term of this patent is extended or adjusted under 35 U.S.C. 154(b) by 199 days.

This patent is subject to a terminal disclaimer.

(21) Appl. No.: 16/084,161

(22) PCT Filed: Feb. 23, 2017

(86) PCT No.: PCT/EP2017/054217
§ 371 (c)(1),
(2) Date: Sep. 11, 2018

(87) PCT Pub. No.: WO2017/153178
PCT Pub. Date: Sep. 14, 2017

(65) Prior Publication Data
US 2019/0175873 A1 Jun. 13, 2019

(30) Foreign Application Priority Data
Mar. 11, 2016 (DE) ...................... 10 2016 204 092.8

(51) Int. Cl.
*A61M 25/01* (2006.01)
*A61B 17/221* (2006.01)
(Continued)

(52) U.S. Cl.
CPC ....... *A61M 25/0136* (2013.01); *A61B 17/221* (2013.01); *A61B 17/2909* (2013.01);
(Continued)

(58) Field of Classification Search
CPC ............... A61M 2025/09125; A61B 17/22031
See application file for complete search history.

(56) References Cited

U.S. PATENT DOCUMENTS 5,219,332 A 6/1993 Nelson et al.
6,551,327 B1 4/2003 Dhindsa
(Continued)

FOREIGN PATENT DOCUMENTS

DE 10 2010 037 618 A1 5/2011
WO WO 2010/133245 A1 11/2010
WO WO 2011/095233 A1 8/2011

OTHER PUBLICATIONS

WO2011095233 Machine Translated, 2011.*
(Continued)

*Primary Examiner* — Wade Miles
*Assistant Examiner* — Mohammed S Adam
(74) *Attorney, Agent, or Firm* — Crowell & Moring LLP

(57) ABSTRACT

A hand-operated functional hose instrument has a hose-like functional part and a wire-like functional part which extends in the hose-like functional part. An operating unit, which is designed for releasable coupling to an operator control handle body, is arranged at a proximal end section of the functional parts and includes two operating parts, which are axially relatively movable and have a hose fixing arrangement or a wire fixing arrangement. The first operating part is axially fixed to the operator control handle body, and the second operating part has a finger-operated operator control slide element. The first operating part has a finger-operated operator control rotary element and/or a distal cone section with an axial recess into which the second operating part can be at least partially inserted, and/or the wire fixing arrangement has two wire fixing parts which can be rotated in relation to one another about a longitudinal axis from a wire release position to a wire clamping position and each have (Continued)

an eccentric axial wire passage opening. The two passage openings are arranged axially one behind the other and are in alignment in the wire release position and are out of alignment in the wire clamping position.

17 Claims, 6 Drawing Sheets

(51) Int. Cl.
*A61B 17/29* (2006.01)
*A61B 17/00* (2006.01)
*A61B 17/22* (2006.01)

(52) U.S. Cl.
CPC . *A61B 17/22031* (2013.01); *A61B 2017/0046* (2013.01); *A61B 2017/00323* (2013.01); *A61B 2017/00477* (2013.01); *A61B 2017/292* (2013.01); *A61M 25/0147* (2013.01)

(56) References Cited

U.S. PATENT DOCUMENTS

| | | |
|---|---|---|
| 2003/0009176 A1 | 1/2003 | Bilitz |
| 2005/0113862 A1 | 5/2005 | Besselink et al. |
| 2005/0240120 A1 | 10/2005 | Modesitt |
| 2012/0088972 A1 | 4/2012 | Pinkowski et al. |
| 2012/0095477 A1 | 4/2012 | Bilitz |
| 2013/0066136 A1* | 3/2013 | Palese ............... A61B 34/73 600/11 |

OTHER PUBLICATIONS

International Search Report (PCT/ISA/210) issued in PCT Application No. PCT/EP2017/054217 dated Jul. 24, 2017 with English translation (ten (10) pages).

German-language Written Opinion (PCT/ISA/237) issued in PCT Application No. PCT/EP2017/054217 dated Jul. 24, 2017 (ten (10) pages).

* cited by examiner

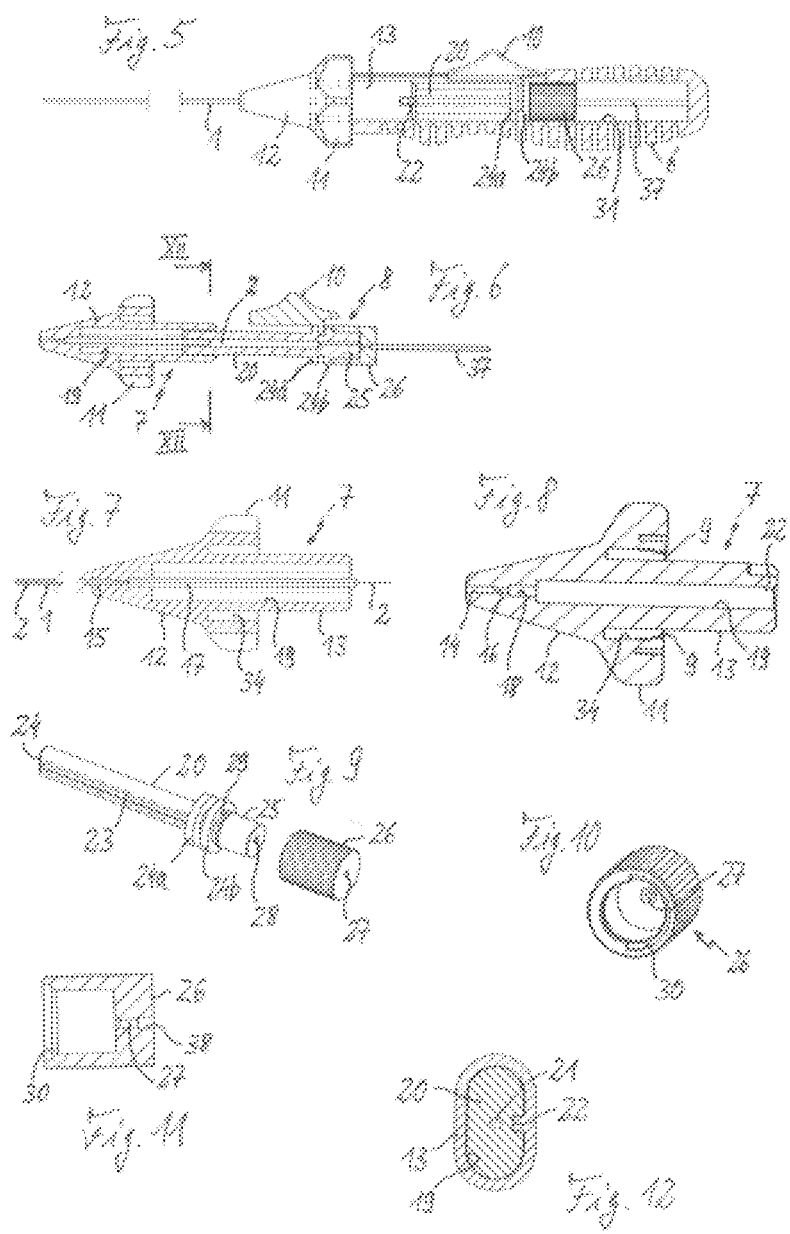

HAND-OPERATED FUNCTIONAL HOSE INSTRUMENT

BACKGROUND AND SUMMARY OF THE INVENTION

The invention relates to a hand-operated functional hose instrument which comprises a hose-like functional part and a wire-like functional part which extends in said hose-like functional part, wherein the two functional parts are axially relatively movable in order to perform a useful function at a distal end. The instrument further includes an operating unit which is designed for releasable coupling to an operator control handle body, is arranged on a proximal end section of the functional parts and comprises a first and a second operating part which are coupled to one another in an axially relatively movable manner, wherein one of the two operating parts has a hose fixing arrangement by way of which the hose-like functional part is fixed to it, and the other of the two operating parts has a wire fixing arrangement by way of which the wire-like functional part is fixed to it. The first operating part includes an axial fixing element for axially fixing the first operating part to the operator control handle, and the second operating part has a finger-operated operator control slide element. Any desired fixing arrangements of a conventional kind, such as adhesive bonding, welding and also releasable and non-releasable interlocking or force-fitting connections, can be used for the hose fixing arrangement and the wire fixing arrangement. The instrument may in particular be an endoscopic functional hose instrument.

In the present context, a hose-like functional part is to be understood generally as any elongate component which has a hollow channel for the passage of the wire-like functional part, wherein said component may be a hose or tube part which is more flexible or more rigid than the wire-like functional part, depending on the application. In the present context, a wire-like functional part is to be understood as any elongate wire-like component which is received in the hollow channel of the hose-like functional part in an axially relatively movable manner and is composed of a metal or plastics material.

Hand-operated functional hose instruments of this and other kinds are customary, for example, in the field of endoscopic medicine, especially in the form of stone-collecting basket instruments with a deployable wire basket for collecting stones or the like in tissue cavities, and also similar instruments, such as wire filter instruments, wire loop instruments and collecting net instruments. In these known applications, a typically deployable element, such as a wire basket, a wire filter, a wire loop or a collecting net, is located at the distal end of the wire-like functional part and, by moving the wire-like functional part axially forward and back relative to the hose-like functional part which surrounds said wire-like functional part, this element is collapsed and retracted into the distal end of the hose-like functional part or is moved out of said hose-like functional part and deployed. A similar application concerns guide wire units for catheter instruments, wherein in this case the wire-like functional part is a so-called tension wire and the hose-like functional part is a hose which surrounds said tension wire and is connected to the tension wire in the distal region. A distal section of the guide wire unit can be deformed in a desired manner, for example bent, by axial relative movement of the tension wire and the hose, see, for example, laid-open publication U.S. 2005/0113862 A1 in this respect.

The axial relative movement is implemented by operator control of the operating unit at the proximal end section of the functional hose instrument. For the purpose of operator control, the functional hose instrument is typically coupled, by way of its proximal operating unit, to an operator control handle. Conventional designs of the operating unit and an associated operator control handle are usually relatively complex in respect of their construction and/or coupling, and the operator control handle is often connected to the operating unit or the two functional parts in a non-releasable manner. In order to achieve an improvement in this respect, laid-open publication WO 2011/095233 A1 proposes a hand-operated functional hose instrument of the generic type mentioned in the introductory part.

Laid-open publication DE 10 2010 037 618 A1 discloses a medical apparatus comprising a flexible catheter, an operating unit adjoining the proximal end of said flexible catheter while said flexible catheter has, at the distal end, a working element which is operated by a tension or pressure element which is guided through the catheter in a rotatable manner. The operating unit can include, for example, a tube with an incorporated elongate hole and a guide sleeve which can slide in the tube and to which the tension/pressure element in the form of a wire is proximally fixed. An annular handle is pushed onto a central sleeve and connected to said central sleeve such that it can be rotated in relation to said central sleeve but cannot be axially displaced, wherein the central sleeve, for its part, is pushed onto the tube and connected to the guide sleeve. An eye-like handle is axially fixed in a rotationally movable manner at the proximal end of the tube in the manner of clamping tongs. The annular handle and the central sleeve are axially displaced on the tube for the purpose of axially displacing the wire. A premounted rotary sleeve which is screwed, by way of its proximal end, onto a distal thread of the tube and which the user can rotate using one hand while he holds the annular handle and the eye-like handle fixed in position with the other hand serves for the purpose of turning the wire.

Laid-open publication U.S. 2012/0095477 A1 discloses a medical stone-collecting basket instrument comprising an operator control handle on which a thumb-operable slide is held in an axially movable manner in order to extend the collecting basket out of a hose or tube and, respectively, to retract it again. In addition, a rotary knob is arranged at the proximal end of the handle, the user, when holding the instrument by way of the operator control handle with one hand, being able to rotate the collecting basket by way of said rotary knob by operating the rotary knob with the other hand.

Patent publication U.S. Pat. No. 5,219,332 A discloses an auxiliary operator control element which can be fitted onto a medical guide wire at any desired location and by way of which the guide wire can be held more effectively for longitudinal or rotary operations. The auxiliary operator control element includes two corresponding tube parts which can be axially plugged together and a locking part which can be received in said tube parts and is composed of an elastomeric material. The tube parts each have a continuous axial slot over their length, it being possible for the guide wire to be inserted through said axial slot. By virtue of relative rotation of the two tube parts, the locking part fixes the guide wire in relation to the tube parts by the locking part being braced between the guide wire and the inner wall of the tube parts so as to deform.

It is an object of the invention to provide a hand-operated functional hose instrument of the kind mentioned in the introductory part which is further improved in relation to the abovementioned prior art and in particular in respect of its functionality and/or its construction.

The invention achieves this and other objects by providing a hand-operated functional hose instrument of the kind mentioned on the outset which comprises further advantageous features.

If required, all of the components of the operating mechanism of the functional hose instrument according to the invention can be produced as plastic parts by injection molding, and mounting of the operator control unit comprising the two functional parts on an associated operator control handle can be implemented quickly and easily and preferably without a tool by releasable coupling. Here, releasable coupling is to be understood as a connection which can be released without being destroyed and can be repeatedly established and released again as required. Production entirely without metal components is also possible, this being useful for medical endoscopy applications in which magnetic resonance technology is used. The separate operator control handle can be manufactured independently of the operator control unit and the two hose- or wire-like functional parts and the design of said operator control handle can be optimized, for example, from ergonomic and handling points of view.

The invention comprises several aspects which are implemented on their own or in any desired combination in addition to the features mentioned on the outset in corresponding embodiments of the invention. In one aspect of the invention, the first operating part has a finger-operated operator control rotary element. This allows a user to rotate the first operating part, and therefore also the hose- or wire-like functional part which is fixed to it, relative to the operator control handle in a convenient manner, for which reason the first operating part is arranged in a rotationally movable manner in relation to the operator control handle body, this involving implementing the axial fixing element of said first operating part in a corresponding rotationally movable manner. In an advantageous implementation, the instrument is designed for one-handed operator control, that is to say it can be operated using only one hand in this case.

In a further aspect of the invention, the first operating part has a distal cone section with an axial recess into which the second operating part can be at least partially inserted. This allows, if required, a comparatively short design for the operating unit and therefore also for the operator control handle. In addition, this measure can assist the axially movable guidance of the two operating parts on one another.

In a further aspect of the invention, the wire fixing arrangement comprises two wire fixing parts which can be rotated in relation to one another about a longitudinal axis from a wire release position to a wire clamping position and each have an eccentric axial wire passage opening, wherein the two passage openings are arranged axially one behind the other and are in alignment in the wire release position and are out of alignment in the wire clamping position. This wire fixing arrangement can be implemented in a simple manner in respect of manufacture and provides a sufficient clamping force for the wire-like functional part in a functionally reliable manner. For the purpose of fixing to the corresponding operating part, the wire-like functional part is inserted, by way of its proximal end section, through the aligned passage openings in the wire release position of the wire fixing parts, after which the wire fixing parts can be rotated to their wire clamping position. The eccentric passage openings move out of alignment as a result, this resulting in bending and deformation of the inserted section of the wire-like functional part and in this way the desired fixedly clamped fixing of the wire-like functional part to the operating part in question.

In a development of the invention, the second operating part has a fixing body, which is coupled to the first operating part in a rotationally fixed and axially movable manner, to which the operator control slide element is coupled in a rotationally movable and axially fixed manner. Owing to this advantageous construction, when the user rotates the first operating part by way of the operator control rotary element, the fixing body of the first operating part rotates at the same time in synchronism, while the operator control slide element does not rotate at the same time and therefore does not change its position relative to the operator control handle in the rotation direction. The fixing body of the first operating part serves for fixing the hose-like or the wire-like functional part, while the other functional part is fixed to the second operating part. This has the advantageous effect that, in the event of the rotational movement which is initiated by the user by way of the operator control rotary element, the hose-like and the wire-like functional part rotate in synchronism. This prevents any frictional losses which could be produced by relative rotation of the two functional parts.

In a development of the invention, one of the two operating parts has a guide sleeve, while the other operating part has a guide element which is guided in said guide sleeve in a rotationally fixed and axially movable manner. This contributes to secure guidance of the two operating parts, which are axially movable relative to one another, on one another.

In a refinement of this measure, the two operating parts have end stops for limiting the axial relative movement of the guide sleeve and the guide element on both sides. As a result, the two axially relatively movable operating parts remain connected to one another in a secured manner even when they are not yet mounted on the operator control handle or when they have been removed from said operator control handle.

In a development of the invention, the two wire fixing parts are formed by a tubular fixing end section of the operating part in question and a fixing connection piece which can be axially plug-connected to said tubular fixing end section. This can be implemented in a simple manner in respect of manufacture and has proven to be advantageous and reliable in respect of functioning. The fixing connection piece needs to be inserted only axially onto or into the fixing end section. In the inserted position, it then needs to be rotated only in a corresponding manner in relation to the fixing connection piece for fixedly clamping or releasing the wire-like functional part.

In a development of the invention, the first operating part has the hose fixing arrangement, while the second operating part includes the wire fixing arrangement. In an advantageous embodiment, the user implements the axial relative movement of the two operating parts by axially displacing the operator control slide element relative to the operator control handle. This then means that the wire-like functional part can be axially moved forward and back in relation to the hose-like functional part in an active manner. In the case of a medical stone-collecting basket instrument, the collecting basket which is provided distally on the wire-like functional part can be moved forward out of the surrounding hose-like functional part and deployed and, respectively, drawn back into said hose-like functional part again in this way.

In an alternative development, the first operating part has the wire fixing arrangement, while the second operating part includes the hose fixing arrangement. In this case, the user can then push the hose-like functional part forward or backward relative to the wire-like functional part, for example by active axial displacement of the operator control slide element relative to the operator control handle. In the case of the mentioned stone-collecting basket instrument, the collecting basket can be deployed by actively drawing back the hose-like functional part and can be collapsed into the hose-like functional part again by pushing the hose-like functional part forward in this way, wherein the wire-like functional part, and therefore also the collecting basket, retains its axial position. This may be advantageous for the process for collecting kidney stones and other particles which are to be removed from an animal or human organism.

In a development of the invention, the operator control rotary element is arranged distally in front of the operator control slide element. This facilitates convenient operator control of the instrument by the user, for example using only one hand, wherein said user can operate, for example, the operator control slide element using the thumb and the operator control rotary element also using the thumb or using the thumb and index finger.

In an alternative development, the operator control rotary element is arranged proximally behind the operator control slide element. This implementation also allows for one-handed operator control of the instrument. To this end, the user holds the operator control handle in the opposite hand position, that is to say with the thumb side of his hand which is holding the handle in the proximal instrument direction instead of the distal instrument direction.

In a development of the invention, the functional hose element comprises an operator control handle comprising a handle body which is designed for releasably receiving the operating unit and has a coupling element for axially fixed coupling of the first operating part. Releasably receiving the operator control unit makes it easier to mount said operator control unit on the operator control handle and allows for simple removal of the operator control unit from the operator control handle and reattachment of said operator control unit or another, in this respect physically identical, operating unit, as required. Owing to the axially fixed coupling of the first operating part to the operator control handle body, when the operator control slide element which is arranged on the second operating part is operated, the second operating part and the functional part which is fixed to it are actively moved forward or backward relative to the operator control handle body, while the first operating part and the functional part which is fixed to it maintain their axial position relative to the operator control handle body.

In a refinement of this measure, the coupling element of the handle body is designed for rotationally movable coupling of the first operating part. When the operator control rotary element is operated, the first operating part, preferably together with the second operating part or a fixing body of said second operating part, can then rotate relative to the operator control handle body.

In another refinement, the handle body has an axial guide for the operator control slide element. This can assist secure guiding of the axial movement of the operator control slide element on the operator control handle body.

In another refinement, the operator control rotary element is arranged at a distal or proximal end side of the handle body. These positions for the operator control rotary element are particularly well suited to one-handed operator control of the instrument.

In a further refinement, the handle body is of multipartite design, wherein it comprises a handle base part and a handle coupling part which can be releasably connected to said handle base part, and wherein the handle coupling part is designed for releasably receiving the operating unit and has the coupling element for coupling the first operating part. This refinement permits comparatively simple assembly of the instrument and provides advantages in respect of manufacture.

In a development of the invention, at least one of the two wire passage openings is an opening which is closed at the circumference. This can contribute to a very good clamping or fixing effect of the wire fixing parts which interact in a wire-clamping manner.

BRIEF DESCRIPTION OF THE DRAWINGS

Advantageous embodiments of the invention are illustrated in the drawings and will be described below. In the drawings:

FIG. 5 shows a partially longitudinally sectioned side view of the instrument part from FIG. 2 in the mounted state in accordance with FIG. 4, FIG. 6 shows a longitudinal sectional view of the operating unit of the instrument from FIG. 1 with two axially movably coupled operating parts, FIG. 7 shows a longitudinal sectional view of a first of the two operating parts from FIG. 6 with the hose-like functional part fixed to it and the wire-like functional part passed through it, FIG. 8 shows a longitudinal sectional view only of the operating part from FIG. 7 in a sectional plane which is perpendicular to that from FIG. 7, FIG. 9 shows a perspective exploded view of two components of a second of the two operating parts from FIG. 6, FIG. 10 shows a perspective view of a sleeve-like wire fixing body from FIG. 9, FIG. 11 shows a longitudinal sectional view through the wire fixing body from FIG. 10, FIG. 12 shows a cross-sectional view along a line XII-XII from FIG. 6.

DETAILED DESCRIPTION OF THE DRAWINGS

Figure 1:
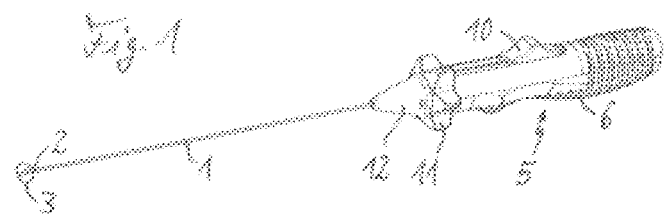
FIG. 1 shows a perspective view of a hand-operated functional hose instrument which can be used as a medical stone-collecting basket instrument.
Figure 2:
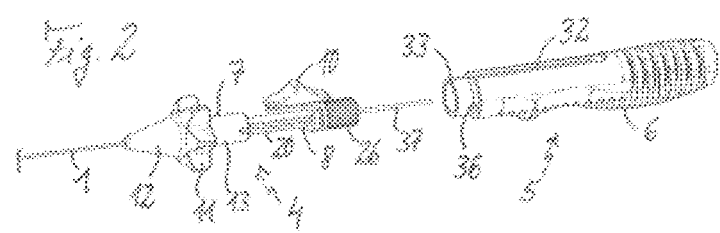
FIG. 2 shows a perspective exploded view of a proximal, operator control-side part of the instrument from FIG. 1.
Figure 3:
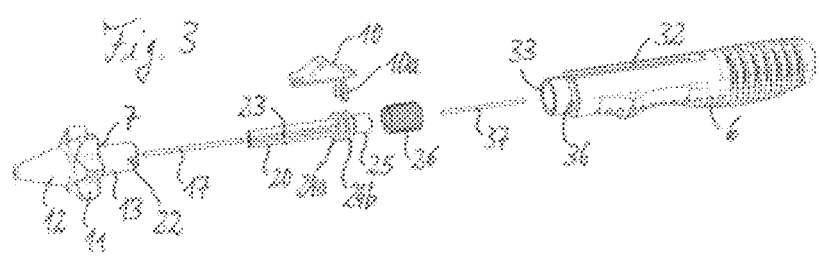
FIG. 3 shows a perspective exploded view of an operating unit and an operator control handle of the instrument from FIG. 1.
Figure 4:
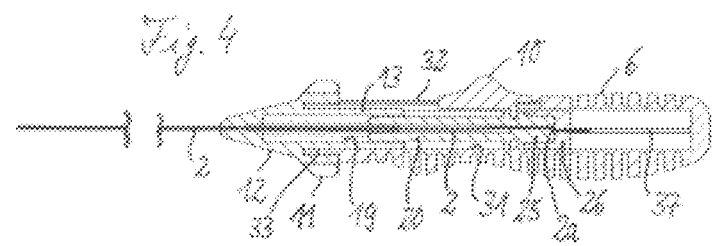
FIG. 4 shows a longitudinal sectional view of the instrument part from FIG. 2 in the mounted state from FIG. 1.

The hand-operated functional hose instrument shown in FIGS. 1 to 14 is designed for use as a stone-collecting basket instrument and includes, as is customary, two elongate functional parts in the form of a hose-like functional part 1, called hose for short, and a wire-like functional part 2, called functional wire for short, which extends in an axially relatively movable manner in said hose-like functional part. Owing to its tensile force functionality, the functional wire 2 is also called a tension wire. The functional wire 2 has, at a front, distal end, a foldable wire basket 3 in order to be able to collect and extract stones or the like, for example in tissue cavities of a patient. This constitutes the useful function in the case of this instrument. The hose 1 and the functional wire 2 can be composed of any suitable plastics or metal materials, as are known for this intended use, for example the hose 1 can be composed of a plastics material and the functional wire 2 can be composed of a superelastic metal material.

In a retracted functional state, the wire basket 3, in a manner retracted at the distal end of the hose 1, is located in the interior of said hose. Owing to axial forward movement of the functional wire 2 relative to the hose 1 and/or axial backward movement of the hose 1 relative to the functional wire 2, the wire basket 3 moves distally out of the hose 1 and is automatically deployed on account of its inherent elasticity. FIG. 1 shows the instrument in this functional state with the wire basket 3 deployed. Owing to the application of tensile force to the functional wire 2 and therefore to the wire basket 3, a collected stone can be securely held in the wire basket 3 in a clamped-in manner. If there are no particles in the wire basket 3, said wire basket can, as required, be collapsed and completely retracted back into the hose 1 by the functional wire 2 being moved axially backward relative to the hose 1 and/or the hose 1 being moved axially forward relative to the functional wire 2.

In order to allow for operation by a user for the purpose of implementing the outlined axial relative movement between the hose 1 and the functional wire 2, the instrument, at its rear, proximal section, has an operating unit 4 and an operator control handle 5, wherein the operating unit 4 can be releasably coupled to the operator control handle 5, especially to a handle body 6 of the operator control handle 5. The operating unit 4 comprises a first operating part 7 and a second operating part 8, wherein the two operating parts 7, 8 are coupled to one another in an axially relatively movable manner. One of the two operating parts 7, 8 has a hose fixing arrangement by way of which the hose-like functional part 1 is fixed to it. The other of the two operating parts 7, 8 has a wire fixing arrangement by way of which the wire-like functional part 2 is fixed to it. The first operating part 7 includes an axial fixing element 9 with the aid of which it can be axially fixed to the operator control handle body 6. The second operating part 8 includes a finger-operated operator control slide element 10.

In the special embodiment according to FIGS. 1 to 14, the first operating part 7 comprises a finger-operated operator control rotary element 11 and a distal cone section 12 and also a proximal guide sleeve section 13, that is to say a section which functions as the guide sleeve 13, wherein said first operating part is of integral design, for example in the form of a plastic injection-molded part, in the example shown.

In the case of the instrument in FIGS. 1 to 14, the hose fixing arrangement is provided on the first operating part 7, for which purpose it has a hose receiving bore 14 at the distal end of its distal cone section 12, the hose 1, by way of its proximal end, being inserted into said hose receiving bore and being held, for example, by an adhesive bond 15 as the hose fixing arrangement. A wire passage bore 16 adjoins the hose receiving bore 14 in the proximal direction, the functional wire 2 further extending through said wire passage bore in the proximal direction through the first operating part 7 when the two functional parts 1 and 2 are mounted on the operating unit 4. A reinforcing tube 17 is optionally provided in the sleeve-like guide section 13 of the first operating part 7, said reinforcing tube being inserted, by way of its distal end, into an associated receiving bore 18 in a fixed manner, said receiving bore being provided in the first operating part 7 in a manner proximally adjoining the wire passage bore 16. The reinforcing tube 17 preferably extends proximally to the rear over the entire length of the guide sleeve section 13. The reinforcing tube 17 can optionally be integrally manufactured with the rest of the first operating part 7, for example by plastic injection molding.

The second operating part 8 includes a guide element which is designed to be guided in a guide sleeve of the first operating part 7 in a rotationally fixed and axially movable manner. To this end, in the case of the instrument in FIGS. 1 to 14, the guide sleeve is formed by the guide sleeve section 13 and an axial region of the first operating part 7 that distally adjoins said guide sleeve section, in order to form an associated guide or receiving bore 19. The bore 19 extends along the guide sleeve section 13 and preferably axially through the operator control rotary element 11 and preferably into the distal cone section 12 up to a prespecifiable length, for example up to a length of at least one quarter or at least one third or at least half the axial length of the distal cone section 12. The extension of the guide bore 19 into the cone section 12 allows for a particularly short construction of the operating unit 7, 8 and of the operator control handle 5 as required.

In the example of the instrument shown in FIGS. 1 to 14, the guide element of the second operating part 8 is formed by a rod-like guide body 20 which has an oval cross section in the embodiment according to FIGS. 1 to 14. Matching this, the associated guide bore 19 has a correspondingly oval-shaped cross section, so that the rod body 20 is guided in the receiving bore 19 in an axially movable manner substantially without play. For mounting purposes, the rod-like guide body 20, with its distal end at the front, is inserted into the associated receiving bore 19 proximally from the rear. The functional wire 2 and the reinforcing tube 17 are received in a central passage bore 21 of the rod-like guide body 20.

In the distal direction, the end of the receiving bore 19 in the distal cone section 12 of the first operating part 7 limits the forward movement of the guide rod body 20 and therefore of the second operating part 8 overall relative to the first operating part 7. In the proximal direction, a stop lug or latching tongue 22 which is formed with a radial spring action at the proximal end of the sleeve-like guide section 13 of the first operating part 7 prevents unintentional movement of the guide rod body 20 completely out of the first operating part 7. To this end, the guide rod body 20 has an outer axial groove 23 which ends at a certain distance in front of the distal end 24 of the guide rod body 20 and into which the lug 22 engages, said lug being pushed radially outward in a spring-elastic manner when the guide rod body 20 is inserted into the receptacle 19. In this way, the two operating parts 7, 8 comprise end stops for limiting the axial relative movement of the guide sleeve and the guide element on both sides.

Therefore, the two operating parts 7, 8 remain held on one another in a premounted manner, even if they are not yet mounted on the operator control handle 5 or have been detached from said operator control handle again. The oval cross section of the guide rod body 20 of the second operating part 8 and the associated guide receptacle 19 in the first operating part 7 provides rotationally fixed coupling of the guide rod body 20 of the second operating part 8 to the first operating part 7 without further measures.

The operator control slide element 10 is held on the guide rod body 20 in an axially fixed and rotationally movable manner. To this end, said guide rod body is provided, in a proximal region, with two axially spaced-apart annular flanges 24a, 24b, the operator control slide element 10 engaging in the space between said annular flanges by way of a semicircular bearing fork 10a which is integrally formed on the bottom side of said operator control slide element. As a result, the operator control slide element 10 is axially fixed to the guide rod body 20, while the guide rod body 20 can rotate without the operator control slide element 10 being forcibly rotated at the same time as a result. It can advantageously be provided that the bearing fork 10a extends over somewhat more than 180° in the circumferential direction and functions as a snap-action or clip element which is snapped or clipped onto the, in this region circular, cross section of the guide rod body 20 and in this way held on the guide rod body 20 in a captive manner.

A wire fixing body 25 is formed behind the annular flanges 24a, 24b at the proximal end of the guide rod body 20, said wire fixing body functioning as a first wire fixing part which interacts with a second wire fixing part 26 for forming a wire fixing arrangement by way of which the wire-like functional part 2, by way of its proximal end, can be releasably fixed to the second operating part 8. In the shown exemplary embodiment of FIGS. 1 to 14, the first wire fixing part 25 is implemented by a tubular end section of the second operating part 8, and the second wire fixing part 26 is formed by a fixing connection piece which can be plug-connected to said first wire fixing part. This fixing connection piece may be, for example, as shown, a fixing sleeve which is open on one side and, at its closed end side, is provided with a passage opening 27 which is eccentric in relation to the sleeve longitudinal axis. In a corresponding manner, the wire passage bore 21 of the guide rod body 20 opens out at its proximal end side with an eccentric wire passage opening 28, wherein the two corresponding wire fixing openings 27, 28 are offset in relation to a longitudinal center axis, which functions as the fixing rotation axis, by the same amount. This has the result that the two openings 27, 28 are in alignment with one another in a specific rotation angle position of the sleeve-like fixing connection piece 26 relative to the corresponding fixing tube connection piece 25, this constituting a wire release position of the wire fixing arrangement formed in this way. In the example shown, the two wire guide openings 27, 28 are designed as openings which are closed at the circumference.

In this wire release position, the proximal end of the wire-like functional part 2 can be pushed through the two openings 27, 28, proximally to the rear for mounting purposes, and distally to the front for removal purposes. The sleeve-like fixing connection piece 26 is placed, by way of its open end side, onto the fixing tube connection piece 25 and can be rotated relative to said fixing tube connection piece in this position. Said sleeve-like fixing connection piece can especially be rotated from the wire release position to a wire clamping position in which the two passage openings 27, 28 are out of alignment. The proximal end piece of the wire-like functional part 2, which proximal end piece is pushed through the two openings 27, 28, is accordingly deformed as a result and, owing to its resulting deformed, bent profile in the region of the two openings 27, 28 which are out of alignment, fixed to the second operating part 8 in a clamping manner.

It has been found that the deformation or bending which that end section of the wire-like functional part 2 undergoes owing to the rotation of the two eccentric passage openings 27, 28 on its own provides a sufficiently high clamping effect which holds the wire-like functional part 2 in a manner securely fixed to the second operating part 8, wherein this wire fixing arrangement withstands the required loading without problems. This also applies particularly when superelastic wire materials are used for the wire-like functional part 2.

In order to define the wire release position and the wire clamping position and to avoid excessive rotation of the sleeve-like fixing connection piece 26 in relation to the fixing tube connection piece 25, suitable rotation-limiting stops are provided on said two parts, in the case shown a stop lug 29 on the fixing tube connection piece 25 and a guide groove 30, which extends over a corresponding angular range, on the sleeve-like fixing connection piece 26, it being possible for the stop lug 29 to move within said guide groove, for example over an angular range of between 90° and 270°.

Figure 13:
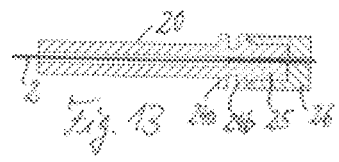
FIG. 13 shows a longitudinal sectional view of the two components from FIG. 9 in the mounted state in a wire release position.
Figure 14:
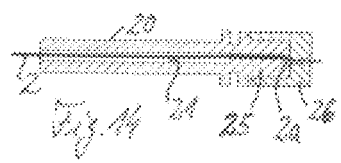
FIG. 14 shows a longitudinal sectional view corresponding to FIG. 13 in a wire clamping position.

FIGS. 13 and 14 illustrate the wire fixing by the two wire fixing parts 25, 26, wherein FIG. 13 shows the wire release position in which the wire passage openings 27, 28 are in alignment, while FIG. 14 shows the wire clamping position in which the wire passage openings 27, 28 are out of alignment and the proximal end of the wire-like functional part 2 is provided with a firmly clamping, fixing bend 2a as a result. Said bend can be reversed by rotating the sleeve-like fixing connection piece 26 back from the wire clamping position to the wire release position, after which the wire-like functional part 2 can be withdrawn from the second operating part 8 again.

The premounted instrument unit comprising the operating unit comprising the first operating part 7, the second operating part 8, the hose-like functional part 1 which is fixed to the first operating part 7, and the wire-like functional part 2 which is fixed to the second operating part 8 can be releasably mounted on the operator control handle body 6 in a very simple manner. The operator control handle body 6 forms a handle shell which is specially shaped in order to be ergonomically held using one hand and which has, in its interior, a receptacle 31, which is open distally at the front, for receiving the operating unit 7, 8. A slot guide 32 is formed on a top side of the handle body 6, the operator control slide element 10 being guided in said slot guide in an axially movable manner, wherein said operator control slide element is held on the handle body 6 in a rotationally fixed manner by this slot guide 32 at the same time.

The first operating part 7 is held on the operator control handle body 6 in a rotationally movable and axially fixed manner. To this end, the operator control handle body 6 has, at its front end, an axial annular projection 33, while an annular recess 34 is correspondingly formed on the first operating part 7 radially between the external rotary element 11 and the inner guide section for the guide rod body 20, it being possible for the axial annular projection 33 of the operator control handle body 6 to be inserted into said annular recess. At the rear end of the axial projection 33, the handle body 6 has a circumferential annular groove 36 which functions as a latching groove and into which the axial fixing element 9 engages in a releasably latching manner, said axial fixing element being formed in the example shown in FIGS. 1 to 14 by one or more latching tongues 9 which are arranged in a manner distributed in the circumferential direction and which protrude radially inward into the annular receiving groove 34. Therefore, the first operating part 7 and, with this, the entire premounted structural unit comprising the first and the second operating part 7, 8 and also the hose-like and the wire-like functional part 1, 2 can be mounted on the operator control handle body 6 in a releasably fixed manner in the axial direction. The annular groove 36 therefore functions as a coupling element for axially fixed coupling of the first operating part 7 to the handle body 6. As an alternative, the latching tongues 9 on the one hand and the annular groove 36 on the other hand swap position, that is to say the annular groove 36 is then formed on the first operating part 7 and the latching tongues 9 are provided on the operator control handle body 6. This prevents the latching tongues 9 from entering the slot guide 32 of the main body 6 and possibly causing a disturbance.

In the mounted state, the first operating part 7 can be rotated relative to the handle body 6, wherein the guide rod body 20 and the wire fixing arrangement 25, 26 are also carried along by this rotational movement, while the operator control slide element 10 is held in the guide slot 32 without rotating at the same time. The user can implement this rotation by corresponding operation of the finger-operated operator control rotary element 11 for example using his thumb while holding the handle body 6 using one hand. As a result, said user can rotate the hose-like and the wire-like functional part 1, 2 synchronously relative to the operator control handle 5.

Furthermore, the user can in particular likewise operate the finger-operated operator control slide element 10 using his thumb by said user moving said operator control slide element axially forward and back relative to the handle body 6. As a result, said user implements, in the example shown in FIGS. 1 to 14, an axial forward movement of the wire-like functional part 2 relative to the handle body 6 and to the hose-like functional part 1 which is axially fixed to it by means of the first operating part 7. Therefore, said user can move the wire basket 3 forward out of the hose 2 at the distal instrument end and deploy said wire basket or collapse said wire basket and move it back into the hose 2. In the case of this axial movement, the second operating part 8 moves forward and back, wherein said second operating part is guided through the guide rod body 20 in the first operating part 7 and through the two radial flanges 24a, 24b in the handle body recess 31, for which purpose said radial flanges have an outside diameter which corresponds to the diameter of the handle body recess 31 and in this way function as a guide or centering ring. For the purpose of axial stroke limiting, a spacer bar 37 is optionally provided, said spacer bar protruding proximally to the rear from the proximal end of the second operating part 8 and limiting the axial movement to the rear by stopping against the rear end of the handle body recess 31. The spacer bar 37 can be mounted, for example, in a receiving bore 38 of the sleeve-like wire fixing connection piece 26, which receiving bore is formed as a widened extension of the eccentric wire passage opening 27.

As is clear from the above explanations, the instrument in FIGS. 1 to 14 is suitable for convenient operation by hand, in particular one-handed operator control, in the case of which the user needs only one hand to operate the instrument, wherein said user can comfortably hold the ergonomically shaped handle body 6 by hand and can operate both the operator control slide element 10 and also the operator control rotary element 11, for example, solely using his thumb.

A few variant embodiments, shown by way of example, of the instrument in FIGS. 1 to 14 will be discussed in the text which follows, wherein, for the purpose of better understanding, the same reference symbols are used for identical and functionally corresponding elements and in this respect reference can be made to the above statements relating to the embodiment in FIGS. 1 to 14 if nothing else is stated.

Figure 15:
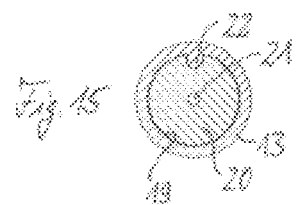
FIG. 15 shows a cross-sectional view corresponding to FIG. 12 for one variant embodiment.
Figure 16:
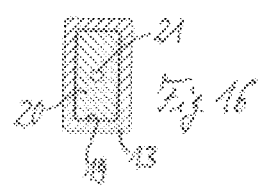
FIG. 16 shows a cross-sectional view corresponding to FIG. 12 for a further variant embodiment.
Figure 17:
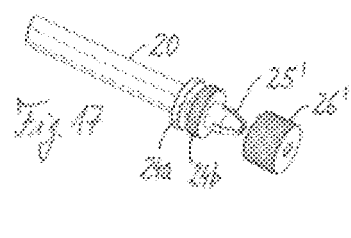
FIG. 17 shows an exploded view corresponding to FIG. 9 for one variant embodiment.
Figure 18:
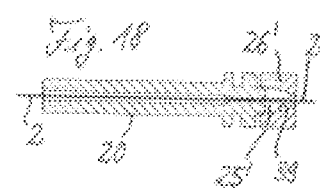
FIG. 18 shows a longitudinal sectional view corresponding to FIG. 14 for the variant embodiment from FIG. 17.

FIGS. 15 and 16 illustrate two variant embodiments in respect of the cross-sectional shape of the guide rod body 20 and the corresponding guide receptacle 19 in the first operating part 7. In the exemplary embodiment from FIG. 15, a round cross section is selected instead of an oval cross section. In this case, the guide lug or latching tongue 22 at the same time serves to connect the guide rod body 20 of the second operating part 8 to the first operating part 7 in a rotationally fixed manner. In the case of the variant embodiment from FIG. 16, a rectangular cross section of the guide rod body 20 and the associated guide receptacle 19 is selected instead of the oval cross section.

FIGS. 17 to 22 illustrate various variant embodiments for the wire fixing arrangement of the wire-like functional part 2 on the second operating part 8 and especially at the proximal end section of the guide rod body 20. To this end, in the exemplary embodiment of FIGS. 17 and 18, a first wire fixing part in the form of an axially slotted tube connection piece 25' which conically tapers proximally to the rear is formed at the proximal end of the guide rod body 20, a sleeve-like fixing connection piece 26' which has a correspondingly tapering tube connection piece receptacle 39 interacting with said tube connection piece. By placing the fixing sleeve 26' onto the fixing tube cone 25', said fixing tube cone is radially compressed in the receptacle 39, as a result of which it firmly holds the passed-through proximal end section of the wire-like functional part 2 in a clamping manner.

Figure 19:
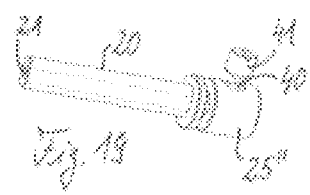
FIG. 19 shows an exploded view corresponding to FIG. 9 for a further variant embodiment.
Figure 20:
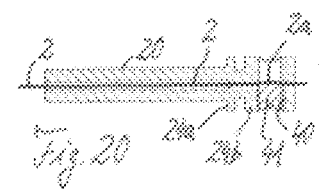
FIG. 20 shows a longitudinal sectional view corresponding to FIG. 14 for the variant embodiment from FIG. 19.

In the exemplary embodiment of FIGS. 19 and 20, the wire fixing includes a tubular end section 25" of the guide rod body 20, which end section is provided with a radial bore 40. As a further wire fixing part, this wire fixing arrangement includes a fixing pin 41 which can be screwed into the radial bore 40 until it reaches a wire clamping position, shown in FIG. 20, in which it butts against the centrally passed-through functional wire and carries along said functional wire in the region of the radial bore 40 and bends said functional wire, so that the wire-like functional part 2 is once again held in a fixedly clamped manner on the guide rod body 20, which functions as a fixing body, by way of a shaped or bent proximal end section 2a.

Figure 21:
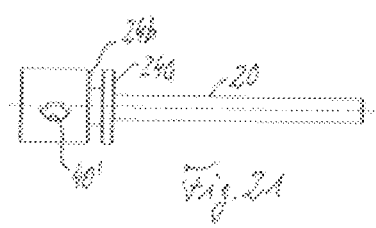
FIG. 21 shows a side view of a further variant embodiment for one of the two components from FIG. 9.
Figure 22:
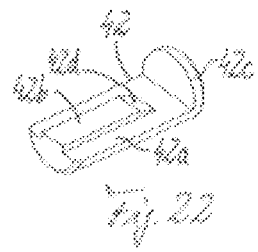
FIG. 22 shows a perspective view of a clamping pin, which matches the component from FIG. 21, as an alternative to the sleeve-like fixing body from FIG. 10.

In the exemplary embodiment of FIGS. 21 and 22, the wire fixing arrangement is implemented in a similar way to that in the example of FIGS. 19 and 20, wherein a plug-in fixing pin 42 is provided instead of the screwable fixing pin 41, said plug-in fixing pin including an insertion body 42a which protrudes from a head part 42c and has an approximately semicircular cross section, a bearing face 42b with a wedge-like run-on face 42d being formed on said insertion body over a certain length. Said pin 42 can be inserted into a radial bore 40' with a correspondingly modified cross-sectional shape, which radial bore is formed, in turn, on the tubular end section 25" of the guide rod body 20. By virtue of running against the wedge face 42d, the functional wire 2 which is guided through the guide rod body 20 can be bent/shaped in its proximal end section in a corresponding manner to that in the exemplary embodiment of FIGS. 19 and 20, wherein said functional wire then rests on the bearing face 42b by way of its bent or shaped region.

Figure 23:
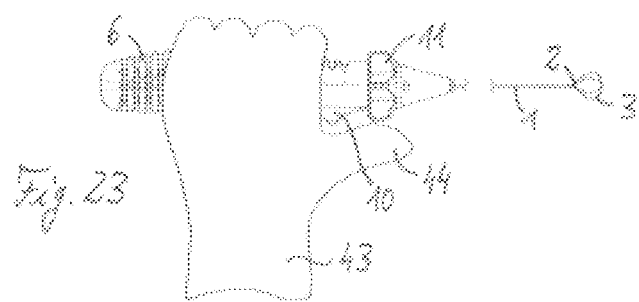
FIG. 23 shows a side view of the instrument from FIG. 1 held for use by a user.

FIG. 23 illustrates the discussed convenient operator control of the instrument in the variant embodiments of FIGS. 1 to 22 using only one hand of the user, with which hand said user can hold the ergonomically shaped handle body 6, wherein said user can preferably operate both the operator control slide element 10 and also the operator control rotary element 11 using his thumb 44.

Figure 24:
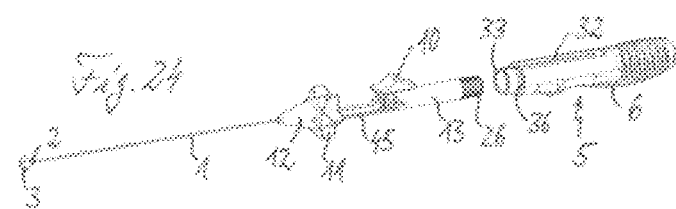
FIG. 24 shows an exploded view corresponding to FIG. 2 for one variant embodiment.
Figure 25:
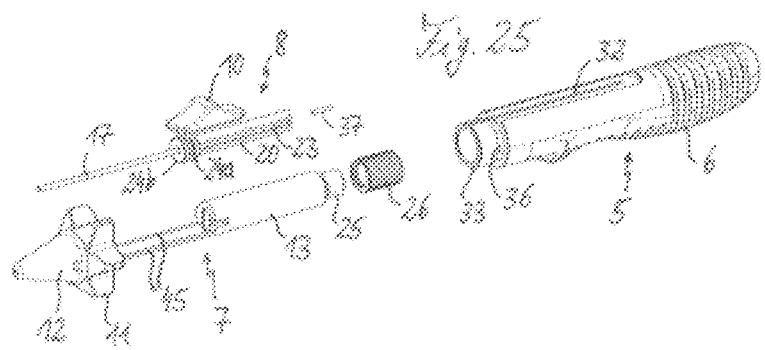
FIG. 25 shows an exploded view corresponding to FIG. 3 for the variant embodiment from FIG. 24.
Figure 26:
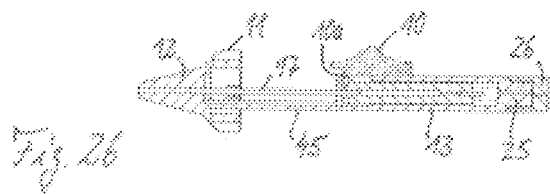
FIG. 26 shows a longitudinal sectional view corresponding to FIG. 6 for the variant embodiment from FIG. 24.
Figure 27:
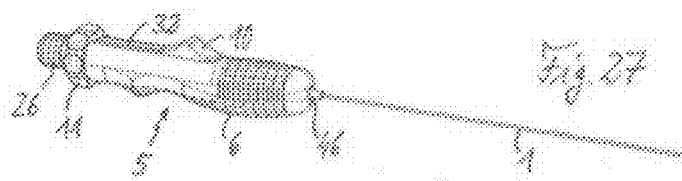
FIG. 27 shows a perspective view corresponding to FIG. 1 for a further variant embodiment.
Figure 28:
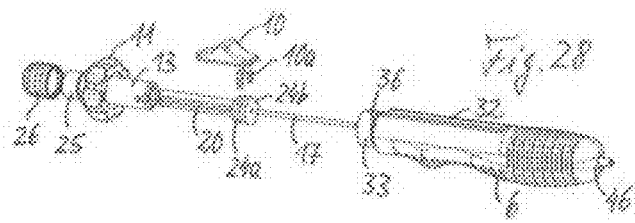
FIG. 28 shows an exploded view corresponding to FIG. 3 for the variant embodiment from FIG. 27.
Figure 29:
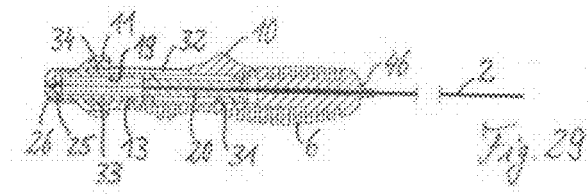
FIG. 29 shows a longitudinal sectional view corresponding to FIG. 4 for the variant embodiment from FIG. 27.

In the exemplary embodiments of FIGS. 1 to 22, the hose-like functional part 1 is fixed to the first operating part 7, while the wire-like functional part 2 is fixed to the operating part 8. FIGS. 24 to 26 illustrate a variant embodiment in which the hose-like functional part 1 is fixed to the second operating part 8, while the wire-like functional part 2 is fixed to the first operating part 7.

To this end, the first operating part 7 is modified to the effect that the guide sleeve section 13 is axially spaced apart from the operator control rotary element 11 and the cone section 12, which distally adjoins said operator control rotary element, and is connected to the operator control rotary element 11 by means of a web section 45 which is preferably integrally formed with the operator control rotary element 11 and the guide sleeve section 13. The wire fixing arrangement comprising the fixing tube connection piece 25 and the sleeve-like fixing connection piece 26 which can be placed on said fixing tube connection piece is formed at the proximal end of the fixing sleeve section 13 of the first operating part 7 in this case, so that the wire-like functional part 2 is fixed to the first operating part 7 there.

The second operating part 8 is modified to the effect that the spaced-apart annular flanges 24a, 24b for rotationally movable axial fixing of the operator control slide element 10 are formed at a front, distal end section of the guide rod body 20, and the axial guide slot 23 ends at a slight distance in front of the proximal end of the guide rod body 20. The hose-like functional part 1 is guided through a corresponding central bore in the cone section 12 and in the operator control rotary element 11 through the same and is fixed by way of its proximal end to and in the guide rod body 20, preferably approximately level with the annular flanges 24a, 24b, for example by an adhesive bond.

Therefore, in this variant embodiment of FIGS. 24 to 26, the user can actively move the hose 1 forward and back in relation to the functional wire 2 by axially operating the operator control slide element 10, while the functional wire 2 remains axially immobile in relation to the operator control handle 5. In this way, the functional wire 2 remains axially immobile in position when the user moves the hose 1 axially backward and as a result the wire basket 3 moves out of the hose 2 and is deployed. Accordingly, the wire basket 3 remains axially in position when the user moves the hose 2 forward again in order to contract the wire basket 3. This can be advantageous for medical stone-collecting applications.

Figure 30:
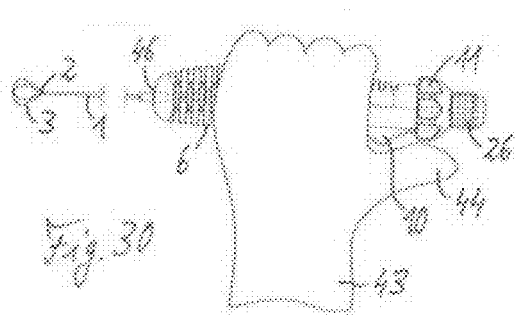
FIG. 30 shows a view corresponding to FIG. 23 for the variant embodiment from FIG. 27.

FIGS. 27 to 30 illustrate an implementation according to the invention in which the hand-operated functional hose instrument is held by the user in a gripping direction which is reversed in relation to that of the above-described examples of FIGS. 1 to 26, as is clear by comparing FIG. 30 with FIG. 23. In the variant embodiment of FIGS. 27 to 30, the operator control rotary element 11 is arranged at the proximal end, instead of the distal end, of the operator control handle body 6 which is modified in this respect. At the distal end, the operator control handle body 6 has an outlet cone 46 from which the hose-like and the wire-like functional part 1, 2 exit in the distal direction. The second operating part 8 is configured as in the exemplary embodiment of FIGS. 23 to 26, wherein the hose-like functional part 1 is again fixed to the fixing rod body 20.

In the variant embodiment of FIGS. 27 to 30, the guide sleeve section 13 protrudes proximally and distally beyond the region of the operator control rotary element 11, wherein its proximal end is configured, as in the exemplary embodiment of FIGS. 23 to 26, as the tube connection piece-like wire fixing part 25 with which the other wire fixing part in the form of the sleeve-like fixing connection piece 26 interacts in order to provide the fixing arrangement by way of which the wire-like functional part 2 is fixed to the first operating part 7.

As shown in FIG. 30, in this variant embodiment, when the user holds the operator control handle body 6 using his hand 43 and can operate the operator control rotary element and the operator control slide element 10 using his thumb 44, the hose-like and the wire-like functional part 1, 2 extend out of the operator control handle 5 from the side of the user's hand which is averted from the thumb, while conversely, in the case of FIG. 23, the two functional parts 1, 2 exit from the operator control handle 5 on the side of the hand which faces the thumb.

Figure 31:
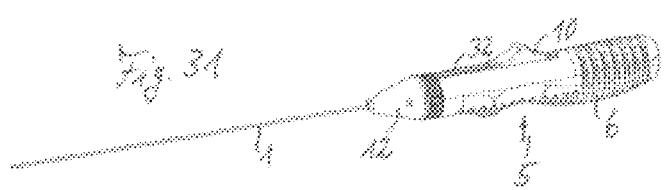
FIG. 31 shows a perspective view corresponding to FIG. 1 for a further variant embodiment.
Figure 32:
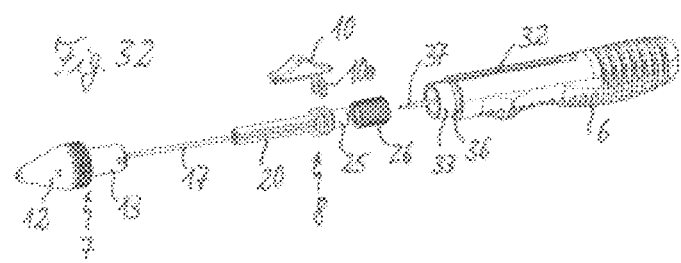
FIG. 32 shows an exploded view corresponding to FIG. 3 for the variant embodiment from FIG. 31.
Figure 33:
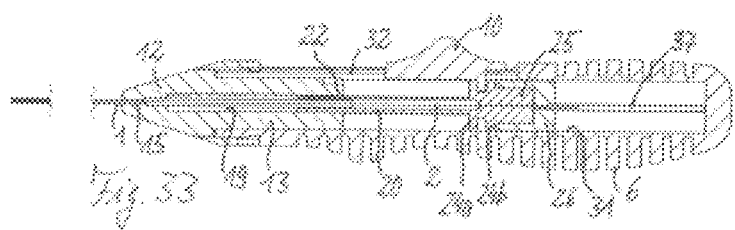
FIG. 33 shows a longitudinal sectional view corresponding to FIG. 4 for the variant embodiment from FIG. 31.

FIGS. 31 to 33 illustrate an exemplary embodiment which corresponds to that of FIGS. 1 to 14 with the exception that the first operating part 7 is implemented without a finger-operated operator control rotary element 11. This variant embodiment is therefore suitable for applications in which there is no need to actively rotate the first operating part 7 in relation to the handle body 6. Otherwise, the instrument of FIGS. 31 to 33 exhibits the same advantageous features and properties as explained above in relation to the exemplary embodiment of FIGS. 1 to 14 to which reference can be made.

Figure 34:
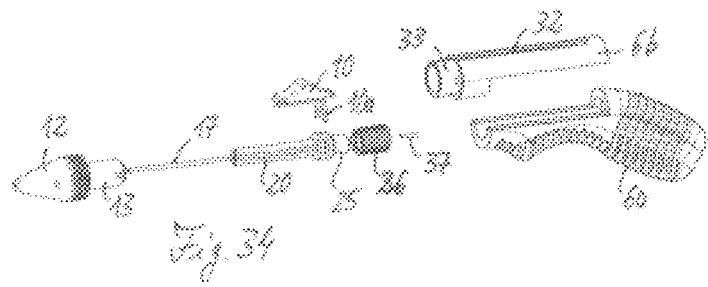
FIG. 34 shows a perspective exploded view corresponding to FIG. 32 for a further variant embodiment.

FIG. 34 shows a variant embodiment which corresponds to that of FIGS. 31 to 33 with the single modification that the operator control handle 6 is configured in two parts with a handle main body or handle base part 6a and an attachment body or handle coupling part 6b which is to be releasably connected to said handle main body or handle base part, wherein the operating unit 7, 8 is mounted on said attachment body or handle coupling part. This can further simplify assembly of the instrument. A two-part handle design of this kind can also be used in the other embodiments of the invention mentioned.

As is clear from the above description of advantageous exemplary embodiments, the invention provides a functional hose instrument which can be produced with relatively little complexity and can be operated in a convenient manner using one hand, wherein the components of said functional hose element can be releasably fitted to one another and removed from one another again in a simple manner. The invention is suitable not only for medical stone-collecting basket instruments as described, but also for other endoscopic functional hose instruments and for any desired other applications which use an instrument of the kind under consideration which are intended to be hand-operated by means of an operator control handle.

What is claimed is:

1. A hand-operated functional hose instrument, comprising:
    a hose-like functional part and a wire-like functional part which extends in said hose-like functional part, wherein the two functional parts are axially relatively movable relative to each other in order to perform a function at a distal end, and
    an operating unit which is designed for releasable coupling to an operator control handle body, is arranged on a proximal end section of the functional parts and comprises a first operating part and a second operating part which are coupled to one another in an axially relatively movable manner relative to each other, wherein
    one of the two operating parts has a hose fixing arrangement by way of which the hose-like functional part is fixed to it, and the other of the two operating parts has a wire fixing arrangement by way of which the wire-like functional part is fixed to it,
    the first operating part has an axial fixing element for axially fixing the first operating part to the operator control handle body,
    the second operating part has a finger-operated operator control slide element, and
    the wire fixing arrangement comprises two wire fixing parts capable of being rotated in relation to one another about a longitudinal axis from a wire release position to a wire clamping position and each have an eccentric axial wire passage opening, wherein the two passage openings are arranged axially one behind the other and are in alignment in the wire release position and are out of alignment in the wire clamping position, wherein the eccentric axial wire passage openings are formed by circumferentially closed openings.

2. The functional hose instrument as claimed in claim 1, wherein the second operating part has a fixing body, which is coupled to the first operating part in a rotationally fixed and axially movable manner, for fixing the associated functional part, wherein the operator control slide element is coupled to the fixing body in a rotationally movable and axially fixed manner.

3. The functional hose instrument as claimed in claim 1, wherein one of the two operating parts has a guide sleeve and the other operating part has a guide element which is guided in said guide sleeve in a rotationally fixed and axially movable manner.

4. The functional hose instrument as claimed in claim 3, wherein the two operating parts have end stops for limiting the axial relative movement of the guide sleeve and the guide element on both sides.

5. The functional hose instrument as claimed in claim 1, wherein the two wire fixing parts are formed by a tubular end section of one of the two operating parts and a fixing connection piece which can be plug-connected to said tubular end section.

6. The functional hose instrument as claimed in claim 1, wherein
    the first operating part has the hose fixing arrangement and the second operating part has the wire fixing arrangement, or
    the first operating part has the wire fixing arrangement and the second operating part has the hose fixing arrangement.

7. The functional hose instrument as claimed in claim 1, further comprising an operator control handle including a handle body which is designed for releasably receiving the operating unit and has a coupling element for axially fixed coupling of the first operating part.

8. The functional hose instrument as claimed in claim 7, wherein the coupling element of the handle body is designed for rotationally movable coupling of the first operating part.

9. The functional hose instrument as claimed in claim 7, wherein the handle body has an axial guide for the operator control slide element.

10. The functional hose instrument as claimed in claim 7, wherein the handle body is of multipartite design, wherein it comprises a handle base part and a handle coupling part which can be releasably connected to said handle base part, and wherein the handle coupling part is designed for releasably receiving the operating unit and has the coupling element for coupling the first operating part.

11. The functional hose instrument as claimed in claim 1, wherein at least one of the two wire passage openings is an opening which is closed at the circumference.

12. The functional hose instrument as claimed in claim 1, wherein it is an endoscopic functional hose instrument.

13. A hand-operated functional hose instrument, comprising:
    a hose-like functional part and a wire-like functional part which extends in said hose-like functional part, wherein the two functional parts are axially relatively movable relative to each other in order to perform a function at a distal end, and
    an operating unit which is designed for releasable coupling to an operator control handle body, is arranged on a proximal end section of the functional parts and comprises a first operating part and a second operating part which are coupled to one another in an axially relatively movable manner relative to each other, wherein
    one of the two operating parts has a hose fixing arrangement by way of which the hose-like functional part is fixed to it, and the other of the two operating parts has a wire fixing arrangement by way of which the wire-like functional part is fixed to it,
    the first operating part has an axial fixing element for axially fixing the first operating part to the operator control handle body,
    the second operating part has a finger-operated operator control slide element,
    the first operating part has a finger-operated operator control rotary element, the operator control rotary element is arranged distally in front of the operator control slide element; and the wire fixing arrangement comprises two wire fixing parts capable of being rotated in relation to one another about a longitudinal axis from a wire release position to a wire clamping position and each have an eccentric axial wire passage opening, wherein the two passage openings are arranged axially one behind the other and are in alignment in the wire release position and are out of alignment in the wire clamping position, wherein the eccentric axial wire passage openings are formed by circumferentially closed openings.

14. The functional hose instrument as claimed in claim 13, further comprising an operator control handle including a handle body which is designed for releasably receiving the operating unit and has a coupling element for axially fixed coupling of the first operating part.

15. The functional hose instrument as claimed in claim 14, wherein the operator control rotary element is arranged at a distal or proximal end side of the handle body.

16. A hand-operated functional hose instrument, comprising:

a hose-like functional part and a wire-like functional part which extends in said hose-like functional part, wherein the two functional parts are axially relatively movable relative to each other in order to perform a function at a distal end, and an operating unit which is designed for releasable coupling to an operator control handle body, is arranged on a proximal end section of the functional parts and comprises a first operating part and a second operating part which are coupled to one another in an axially relatively movable manner relative to each other, wherein one of the two operating parts has a hose fixing arrangement by way of which the hose-like functional part is fixed to it, and the other of the two operating parts has a wire fixing arrangement by way of which the wire-like functional part is fixed to it, the first operating part has an axial fixing element for axially fixing the first operating part to the operator control handle body, the second operating part has a finger-operated operator control slide element, the first operating part has a distal cone section with an axial recess into which the second operating part can be at least partially inserted; and the wire fixing arrangement comprises two wire fixing parts capable of being rotated in relation to one another about a longitudinal axis from a wire release position to a wire clamping position and each have an eccentric axial wire passage opening, wherein the two passage openings are arranged axially one behind the other and are in alignment in the wire release position and are out of alignment in the wire clamping position, wherein the eccentric axial wire passage openings are formed by circumferentially closed openings.

17. The hand-operated functional hose instrument as claimed in claim 16, wherein the hand-operated functional hose instrument is an endoscopic functional hose instrument.

* * * * *